United States Patent [19]

Strauss

[11] Patent Number: 5,201,736
[45] Date of Patent: Apr. 13, 1993

[54] MAXILLOFACIAL BONE CLAMP

[76] Inventor: Sorrell I. Strauss, 1890 Northwest River Trail, Stuart, Fla. 34994

[21] Appl. No.: 819,811

[22] Filed: Jan. 13, 1992

[51] Int. Cl.⁵ .................................................. A61C 8/00
[52] U.S. Cl. ..................................... 606/69; 433/123; 433/174
[58] Field of Search ..................... 606/69–71; 433/173, 176, 174, 175

[56] References Cited

U.S. PATENT DOCUMENTS

| | | |
|---|---|---|
| 2,112,007 | 3/1938 | Adams . |
| 3,082,525 | 3/1963 | Christensen . |
| 3,436,826 | 4/1969 | Edelman ...................... 433/173 X |
| 3,579,829 | 5/1971 | Sampson . |
| 3,641,671 | 2/1972 | Roberts . |
| 3,741,205 | 6/1973 | Markolf et al. ................... 606/69 X |
| 3,842,442 | 10/1974 | Kolbel . |
| 3,889,375 | 6/1975 | Roberts . |
| 4,038,704 | 8/1977 | Ring . |
| 4,040,129 | 8/1977 | Steinemann et al. . |
| 4,121,340 | 10/1978 | Patrick . |
| 4,202,099 | 5/1980 | Roberts . |
| 4,253,833 | 3/1981 | Edelman ........................ 433/173 |
| 4,379,694 | 4/1983 | Riess . |
| 4,439,152 | 3/1984 | Small ............................ 433/173 |
| 4,522,596 | 6/1985 | Ashkinazy . |
| 4,571,185 | 2/1986 | Rota . |
| 4,728,330 | 3/1988 | Comparetto . |
| 4,741,698 | 5/1988 | Andrews . |
| 4,784,608 | 11/1988 | Mays . |
| 4,787,851 | 11/1988 | Kusano et al. . |
| 4,826,434 | 2/1989 | Krueger ........................ 433/174 |
| 4,828,492 | 5/1989 | Agnone . |
| 4,878,915 | 11/1989 | Brantigan .................... 606/61 X |
| 4,959,065 | 9/1990 | Arnett et al. .................. 606/69 |
| 4,964,801 | 10/1990 | Kawahara et al. . |
| 4,968,250 | 11/1990 | Small . |
| 5,052,930 | 10/1991 | Lodde et al. ................. 433/173 |

FOREIGN PATENT DOCUMENTS

| | | | |
|---|---|---|---|
| 290138 | 11/1988 | European Pat. Off. .............. 606/69 |
| 3732128 | 4/1989 | Fed. Rep. of Germany ...... 433/173 |
| 1037911 | 8/1983 | U.S.S.R. .................................. 606/69 |
| 2091105 | 7/1982 | United Kingdom ................... 606/69 |

Primary Examiner—Robert A. Hafer
Assistant Examiner—Sam Rimell
Attorney, Agent, or Firm—Cushman, Darby & Cushman

[57] ABSTRACT

A maxillofacial bone clamp for attachment to a maxillofacial bone includes an engaging element for engaging the maxillofacial bone and a threaded fastener for engaging the engaging element and attaching it to the maxillofacial bone. The engaging element includes an appliance receptor to which a dental appliance is attachable.

15 Claims, 4 Drawing Sheets

MAXILLOFACIAL BONE CLAMP

BACKGROUND OF THE INVENTION

1. Field of the Invention

The present invention relates to a maxillofacial bone clamp (MBC) attachable to the zygomatic process of the maxilla and specific edentulous areas of the body of the mandible to provide various functions. These include stabilization of certain maxillofacial fractures, maxillofacial osteoplasties, and surgical defects of the maxilla and mandible. In addition, the MBC may provide a substructure upon which to attach dental and maxillofacial type implant abutments for reconstruction with removable prostheses.

2. Background Information

A. Maxillofacial Fractures

Many instances of maxillofacial fractures require treatment, including the repositioning and direct stabilization of displaced bone fragments. Most surgical instruments utilized to reposition facial fractures are bulky and require removal once the fragments are stabilized.

B. Maxillofacial Osteoplasties

Maxillofacial osteoplasties involve the surgical sectioning, repositioning and stabilization of certain bones or bony segments of the maxillofacial region. These fragments are often stabilized with metal bone plates and/or screws. Occasionally, these appliances are difficult to manipulate until initially secured to one stable point. Frequently, maxillofacial osteoplasty procedures require the placement of various apparatus for pre-osteoplasty reference points to assist in accuracy with placement of mobilized maxillofacial bone fragments and/or joint position following surgery.

C. Surgical Defects of the Maxilla and Mandible

Surgical defects of the maxilla are usually replaced by removable prosthesis. These are frequently difficult to stabilize due to loss of major bone segments. Surgical defects of the mandible frequently result in very unstable, mobile bone fragments, and lower facial collapse. These fragments are often stabilized with internal metal plates or external pins connected by plastic bars.

D. Implants

Dental implants in various forms are increasingly widely used and have been available for many years. These implants are utilized to replace missing teeth by providing support or attachments for dental appliances, either removable or nonremovable. Heretofore, the implants have been attached to either the maxilla or to the mandible with the majority of these implants falling into one of three categories: subperiosteal, transosteal, and endosteal.

Subperiosteal implants usually include a perforated metal form designed to rest on the superior surface of cortical bone of the mandible or the inferior surface of the maxilla. They are covered by periosteum and rely on accurate adaption to the surface of the bone for proper healing and stabilization. Projections passing through the oral mucosa provide attachment points for the dental applicants.

Transosteal implants are used with the mandible. A large metal is placed a the inferior border of the mandible through a cutaneous approach and multiple pins extend through the plate into the inner surface of the bone, some of which can protrude entirely through the superior surface of the one to provide attachment points for the dental appliances.

Endosteal type implants include endosteal blades, ramus frames and more recently, cylinders. Endosteal blades are metal plates inserted intraorally through the mucosa for attachments. the ramus frame is a large one piece framework used almost exclusively to restore only the mandible. It includes a large blade at the anterior portion of the mandible and extensions running bilaterally into the ramus of the mandible for support. Cylinders may be threaded or nonthreaded, solid or hollow and are placed through the superior surface of the mandible or inferior surface of the maxilla at the creased of the ridge and extended up into solid bone. They are usually left covered in place for three to six months to allow for osseointegration or fusion to the surrounding bone. After this period, they are uncovered at the crest of the ridge so that dental applicants can be attached.

One limitation with these conventional dental implants is that they all attach to the maxilla or mandible. However, the maximal and mandible are subject to radical changes over the life of the individual, undergoing varying degrees of shrinkage with age, tooth loss and disease.

The conventional devices are frequently inapplicable to a person missing a small or large segment of the maxilla or mandible. These persons with major midface skeletal losses are frequently unable to speak properly, masticate and function normally in society.

One object of the present invention is to assist in repositioning maxillofacial bone fractures and to then become an integral part of the permanent stabilization apparatus, thereby eliminating possible cumbersome, time consuming procedures currently utilized. The MBC offers both a "handle" to assist in repositioning bony segments and a stable point from which to attach bone plates. Further, the MBC may be utilized as reference points to assist in accurately positioning bone fragments and joints, thereby reducing additional time consuming operative procedures. It would then become an integral part of the stabilization mechanism as mentioned above. The maxillofacial bone clamp can also be used for stabilization of segmented bone after osteoplasty procedures such as a saggital split osteotomy of the mandible.

Another object of the MBC is to provide an anchorage to assist in stabilization of a maxillofacial prosthesis in this region. The MBC not only provides an intraoral stabilizing mechanism for certain surgical defects of the mandible, but also without additional procedures provides a stable support for removable prosthetic reconstruction.

A further object of the present invention is to provide a device which acts as a substructure for stable attachments of dental and/or maxillofacial appliances. These can be utilized even in the severely resorbed and/or deformed maxilla and mandible. The design of the MBC utilizes available bone in the zygomatic process of the maxilla, which no other known implant or device specifically utilizes. In addition, variations on the MBC are designed for use in mandibles too small or too resorbed to support most known dental implant devices.

SUMMARY OF THE PRESENT INVENTION

The present invention is a maxillofacial bone clamp designed for attachment to edentulous spans of the mandible and to the zygomatic process of the maxilla, also referred to as the malar process of the maxilla or the zygomatic buttress. This is the portion of the skull that connects the maxilla to the zygomatic bone. The zygomatic process is susceptible to far less change over the life of the individual than either the maxilla or the mandible, and therefore, provides a stable bone base to which the maxillofacial bone clamp can be attached.

The maxillofacial bone clamp includes an arch shaped portion with an anterior wing and a posterior wing for conforming to an anterior cortical surface and a posterior cortical surface, respectively, of the zygomatic process. The clamp further includes a threaded appliance receptor to which a handle used for insertion is attached. This handle may be used for certain maxillofacial fracture or osteoplasty segment manipulation. The handle would then be replaced with a bone plate anchored to the clamp and surrounding bone fragments for stabilization. In addition, the site may be utilized by attaching standard implant attachments, hereinafter referred to as abutments, thereby providing a stable substructure for removable dental and/or maxillofacial prosthesis. The clamp is secured to the zygomatic process or mandible with at least one threaded fastener. Due to the positive attachment with the threaded fastener, the maxillofacial clamp can be loaded immediately, unlike many of the conventional implants.

The maxillofacial bone clamp is designed specifically for attachment to the zygomatic process of the maxilla and edentulous spans of the superior surface of the mandibular body. Its uses include, but are not limited to, reduction and stabilization of maxillofacial fractures, manipulation and stabilization of maxillofacial osteoplasties, substructure attachments for dental implant and maxillofacial implant abutments and stabilization of residual maxillary and mandibular defects following traumatic or surgical loss of bone segments.

With the foregoing in mind, other objects, features and advantages of the present invention will become more apparent upon consideration of the following description and the appended claims with reference to the accompanying drawings, all of which form part of this specification, wherein like reference numerals designate corresponding parts in the various figures.

DETAILED DESCRIPTION OF THE INVENTION

Figure 5:
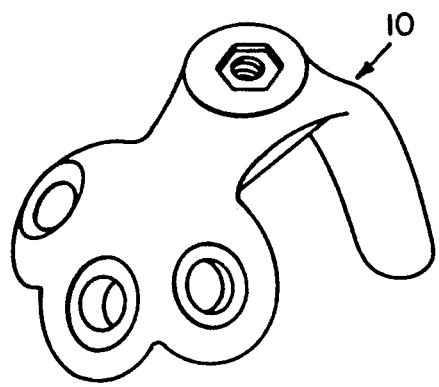
FIG. 5 is a perspective view of an alternative embodiment of the present invention.

FIGS. 1–4 show the maxillofacial bone clamp generally at 10 which includes an arch 12 connecting an anterior wing 14 with a posterior wing 16. An appliance receptor 18 is included in the arch 12 and includes a threaded bore 20 to which dental appliances, appliance attachment devices, or manipulating tools can be threadably attached. The anterior wing 14 includes two bores 22, each for engaging a threaded fastener and attaching the maxillofacial bone clamp 10 to the bone. A stabilizing ridge 23 extends from arch 12 and is used to both strengthen the bone clamp 10 and to provide lateral stability to the bone clamp 10 when it is engaged in a crestal groove cut into the bone. Alternatively, the ridge 23 can be deleted. FIG. 5 shows an alternative embodiment of the bone clamp 10 which is attached to the bone with three threaded fasteners.

Figure 7:
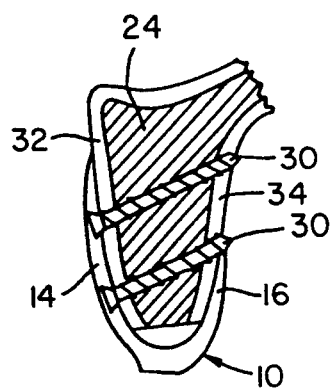
FIG. 7 is a sectional view along line 7—7 in FIG. 6 of the attachment of the present invention to the zygomatic process.
Figure 6:
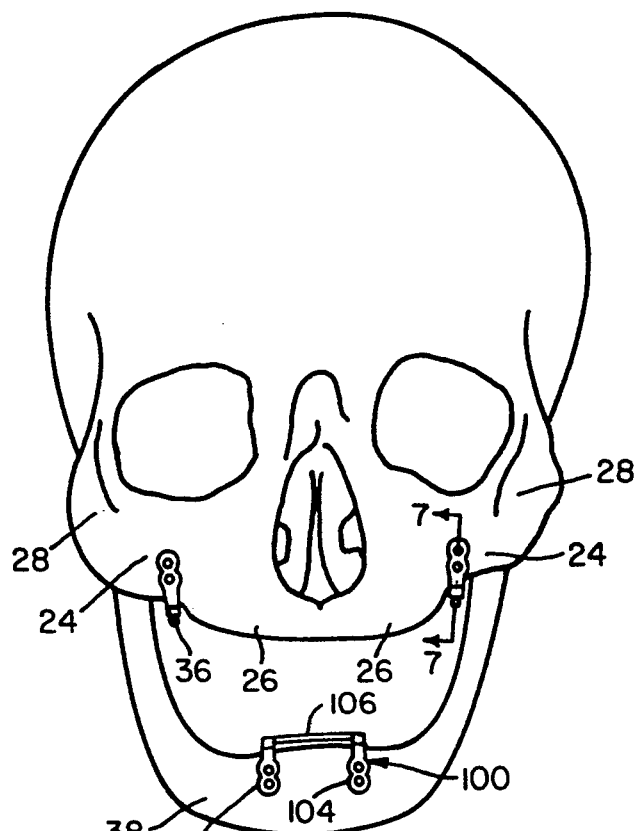
FIG. 6 is a front elevational view of alternative embodiments of the present invention attached to the zygomatic processes and mandible.

As can be seen in FIGS. 6 and 7, the maxillofacial bone clamp 10 can be attached to the zygomatic process of the maxilla 24, the portion of bone connecting the maxilla 26 with the zygomatic bone 28. The maxillofacial bone clamp 10 can also be similarly attached to the maxilla 26 or mandible 38. Two bicortical screws 30 engage the bores 22 and thread into the facial cortex 32 and antifacial cortex 34 of the zygomatic process 24, placing the anterior wing 14 in compression between the screw heads and the bone. The two bicortical screws 30 anchor the maxillofacial bone clamp 10 to the zygomatic process 24, preventing rotation of the maxillofacial bone clamp 10 and allowing immediate loading of the maxillofacial bone clamp 10. Although the screws 30 are shown to be generally parallel to each other, in an alternative embodiment, they can be splayed, either toward or away from each other. Further, more than two screws 30 can be used as well as unicortical screws in alternative embodiments.

The maxillofacial bone clamp can be made of a malleable material such as a titanium alloy, so that the anterior and posterior wings can be formed to closely conform to the shape of the bone. This forming of the wings can be done with the help of a crimping tool that crimps the maxillofacial bone clamp 10 around the bone. This closely conforming shape and arch design that engages or at least partially encases the bone combines with the use of two or more bicortical screws to provide a strong, stable fixation which can be loaded immediately. To increase the stability even further, a crestal groove can be created in the zygomatic process at the time of surgery such that the stabilizing ridge 23 rests in and is antirotationally supported by the groove.

a conventional attachment device 36 can be threaded into the bore 20 to provide an attachment point for conventional dental applicants and prosthetic deices. However, the appliance receptor 18 can be adapted as necessary to provide an attachment point for any conventional type of dental appliance.

Figure 1:
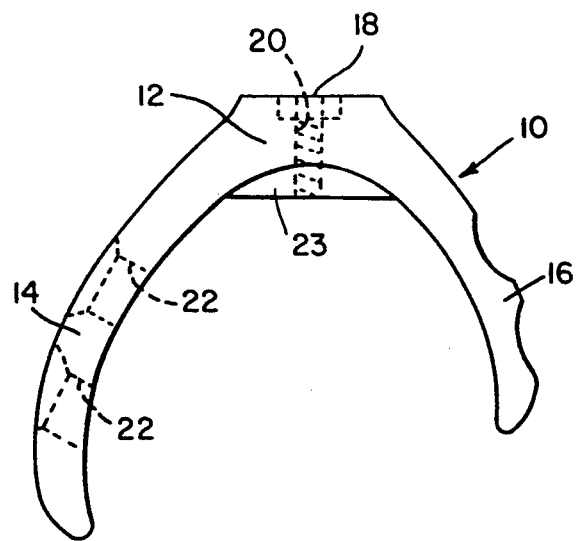
FIG. 1 is a side elevational view of the present invention.
Figure 2:
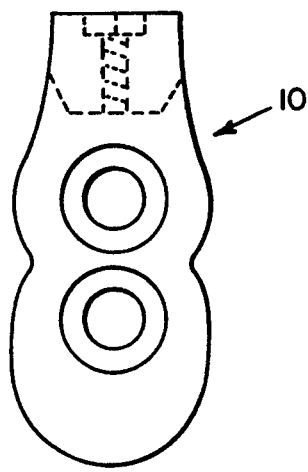
FIG. 2 is a front elevational view of the present invention.
Figure 3:
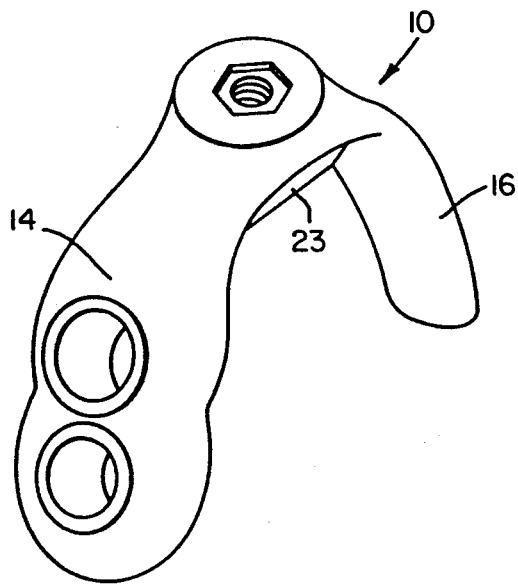
FIG. 3 is a perspective view of the present invention.
Figure 4:
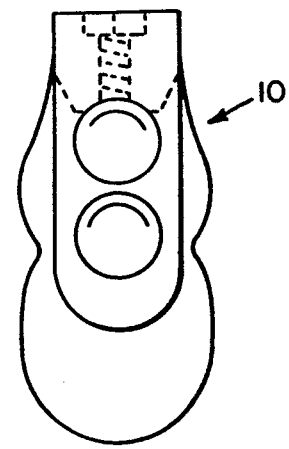
FIG. 4 is a rear elevational view of the present invention.
Figure 8:
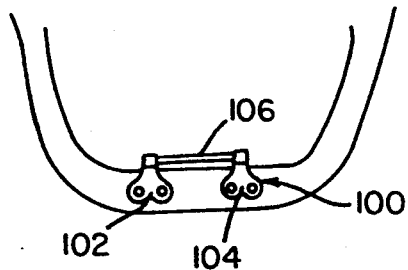
FIGS. 8 is a front elevational view of an alternative embodiment of the present invention.
Figure 9:
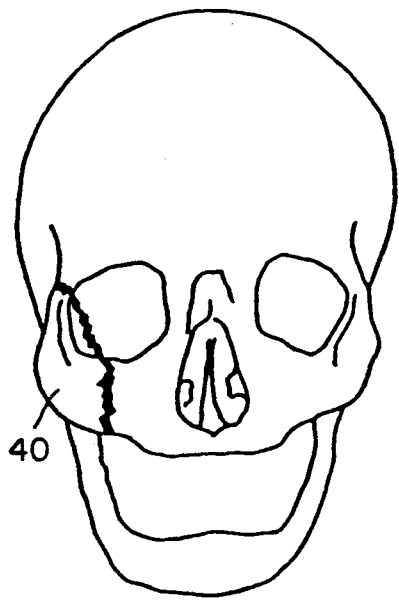
FIGS. 9–16 show alternative uses of the present invention.
Figure 10:
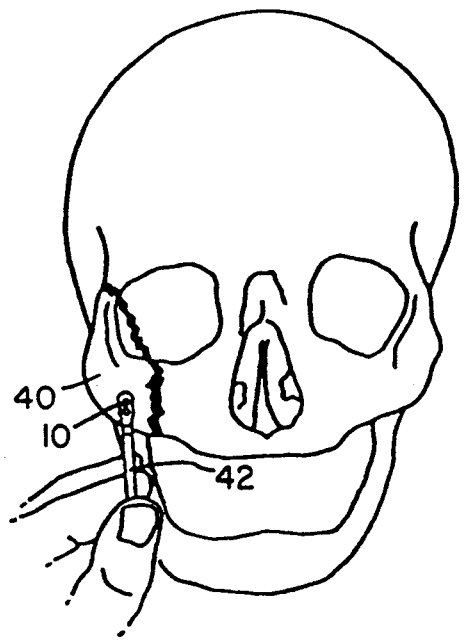
Figure 11:
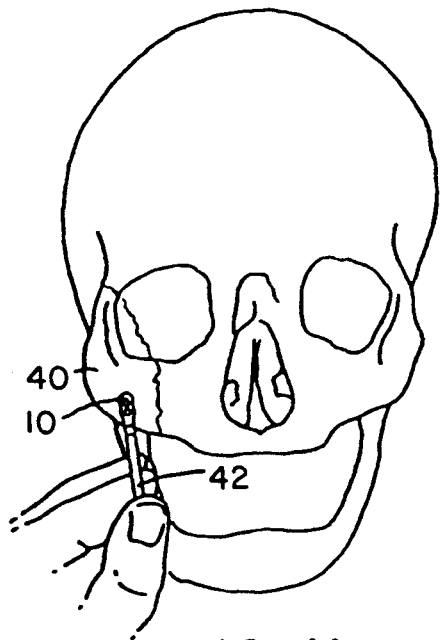
Figure 14:
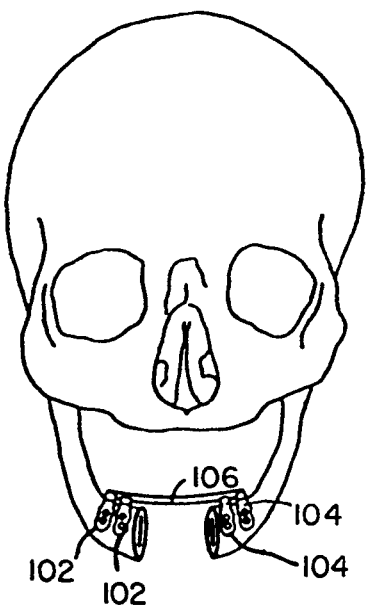

IN alternative embodiments shown in FIGS. 6 and 8, a maxillofacial been clamp 100 includes two arch and wing portions 102 and 104 attached to each other by a center bar 106. The center bar 106 provides an attachment point for the dental appliance. While this embodiment is shown attached to the mandible 38, it can also be attached to the maximal 26 or zygomatic process 24. Additionally, multiple wing portions can be used to further stabilize the center bar 106, as shown in FIG. 14, for instance, when a portion of the mandible has been removed.

the maxillofacial bone clamp 10 can be constructed in various sizes to provide a full range of adaptability to different applications. It can be constructed from any conventional material, including titanium, titanium alloy and surgical stainless steel. Metal spray and hydroxylapatite can be used in conjunction with the maxillofacial bone clamp to promite a bony union between bone clamp and the bone. The wings need not extend in a straight manner as viewed for the anterior to posterior (as shown in FIG. 2) but can e curved to allow more flexibility in attaching to the bone while properly positioning the appliance receptor.

Figure 12:
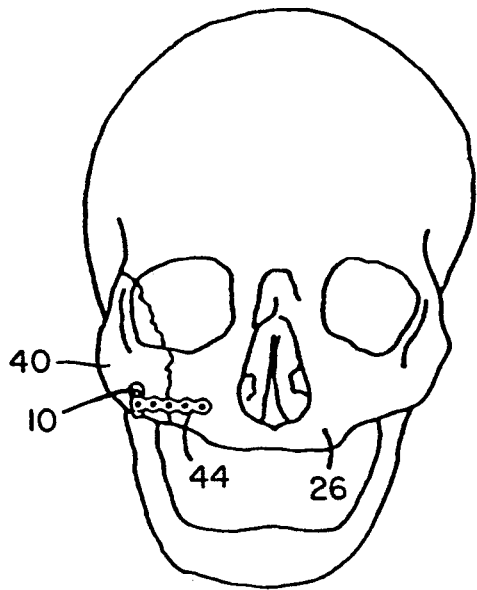
Figure 13:
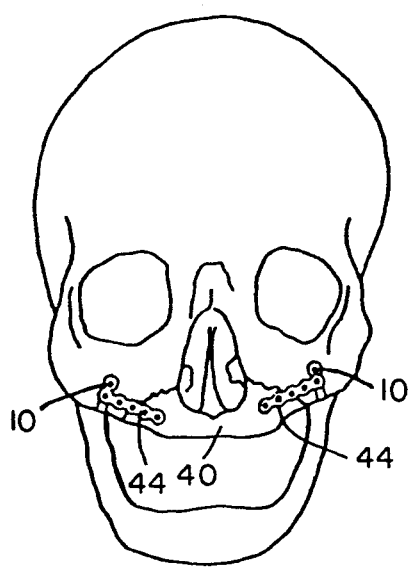
Figure 15:
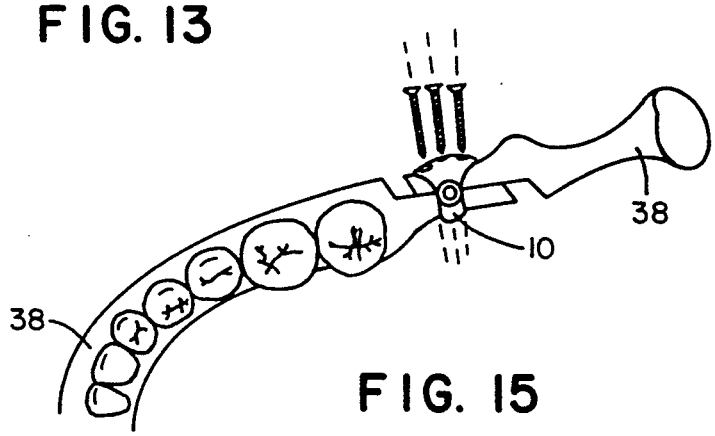
Figure 16:
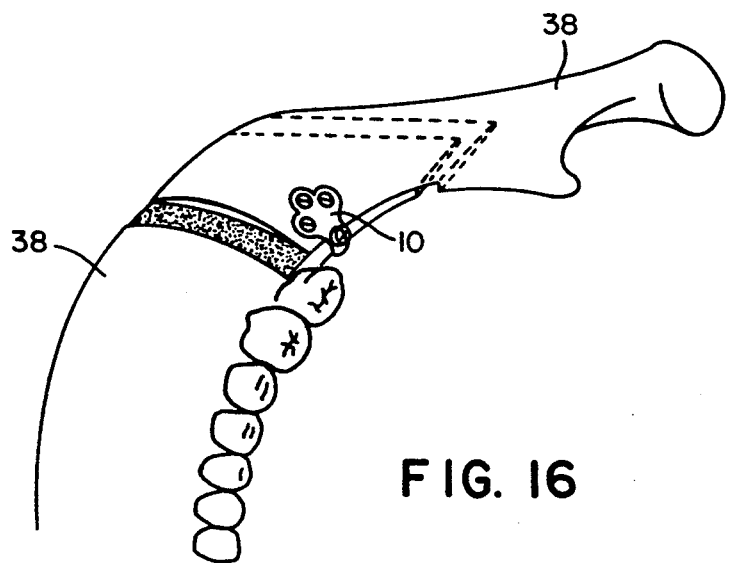

As seen in FIGS. 9–12, the maxillofacial bone clamp 10 can be sued to manipulate and position one segments. The bone clamp 10 is first attached to the bone segment 40. A manipulating handle 42 can hen be attached to the appliance receptor to allow manipulation and positioning of the bone segment. The bone segment 40 can then be immobilized with at least one bone stabilization link 44 attached to a stable portion of bone, for instance the maxilla 26 as shown in FIG. 12, or the zygomatic processes 24 as shown in FIG. 13 and either the bone clamp 10 or the bone segment 40. Further, two or more stabilization links 44 can also be utilized with two or more bone clamps 10, as shown in FIG. 13. FIGS. 15 and 16 are top elevational and perspective views, respectively, showing the maxillofacial bone clamp 10 being used in conjunction with a saggital split osteotomy of the mandible. Such a procedure is used to either lengthen or shorten the mandible. The maxillofacial bone clamp 10 clamps together and stabilizes the two split segments of the mandible 38. In this embodiment, the appliance receptor 18 can e deleted.

While the intention has been described in accordance with what is presently conceived to be the most practical and preferred embodiment, it is to be understood that the invention is not to be limited to the disclosed embodiment but on the contrary, is intended to cover various modifications and equivalent arrangements included within the spirit and the scope of the appended claims, which scope is to be accorded the broadest interpretation of such claims so as to encompass all such equivalent structures.

What is claimed is:

1. A maxillofacial bone clamp for attachment to a maxillofacial bone, comprising:
    means for engaging the maxillofacial bone, the means for engaging comprising arch with a facial wing and a posterior wing for conforming to a facial cortical surface and an antifacial cortical surface, respectively, of the maxillofacial bone or clamping the maxillofacial bone between the facial wind and the posterior wing;
    a stabilizing ridge extending from a concave side of the arch between the facial wind and the posterior wing and connected to a concave portion of at least one of the facial wing and the posterior wing for strengthening the bone clamp and for antirotationally engaging a crestal groove in the maxillofacial bone; and
    at least one threaded fastener for engaging the engaging means and attaching the engaging means to the maxillofacial bone.

2. A maxillofacial bone clamp as in claim 1 wherein the threaded fastener comprises a bicortical screw for threading into the maxillofacial bone.

3. A maxillofacial bone clamp as in claim 2 wherein the maxillofacial bone is a zygomatic process and the bicortical screw attaches the bone clamp to the zygomatic process only from a facial side of the zygomatic process.

4. A maxillofacial bone clamp as in claim 2 wherein h bicortical screw engages at lest one of the anterior and posterior wings.

5. A maxillofacial bone clamp as in claim 1 wherein the means for engaging comprises a malleable metal which is formable to provide a close fit between the means for engaging and the maxillofacial bone.

6. A maxillofacial bone clamp as in claim 1 wherein a plurality of threaded fasteners are used to attach the engaging means to the maxillofacial bone.

7. A maxillofacial bone clamp as in claim 6 wherein at least two of the threaded fasteners are splayed toward each other.

8. A maxillofacial bone clamp as in claim 6 wherein at least two of the threaded fasteners are splayed away from each other.

9. A maxillofacial bone clamp as in claim 1 wherein the stabilizing ridge is connected to both the facial wing and the posterior wing to strengthen the bone clamp.

10. A maxillofacial bone clamp as in claim 1 and further comprising:
    stabilizing link for attaching the maxillofacial bone clamp to another maxillofacial bone.

11. A maxillofacial bone clamp as in claim 1 and further comprising:
    a central bar portion for attachment to at least one other maxillofacial bone clamp to form a bridge over a section of maxillofacial bone when both maxillofacial bone clamps are attached to the maxillofacial bone.

12. A maxillofacial bone clamp as in claim 1, wherein the means for engaging further comprises:
    an appliance receptor to which a dental appliance is attachable.

13. A maxillofacial bone clamp as in claim 12 wherein the appliance receptor comprises a threaded bore to which the dental appliance can be attached.

14. A maxillofacial bone clamp as in claim 12 wherein the dental appliance is a prosthetic device.

15. A maxillofacial bone clamp as in claim 12 wherein the dental appliance is a manipulating device.

* * * * *